(12) United States Patent
Schuermann (10) Patent No.: US 10,226,559 B2
(45) Date of Patent: *Mar. 12, 2019

(54) GUIDEWIRE SYSTEM AND METHOD OF PUMP INSTALLATION USING SAME

(71) Applicant: HeartWare, Inc., Miami Lakes, FL (US)

(72) Inventor: James Schuermann, Dover, MA (US)

(73) Assignee: HeartWare, Inc., Miami Lakes, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/646,433

(22) Filed: Jul. 11, 2017

(65) Prior Publication Data

US 2017/0304514 A1   Oct. 26, 2017

Related U.S. Application Data

(63) Continuation of application No. 14/969,805, filed on Dec. 15, 2015, now Pat. No. 9,717,831.
(Continued)

(51) Int. Cl.
| | | |
|---|---|---|
| *A61M 1/12* | (2006.01) | |
| *A61M 1/10* | (2006.01) | |
| *A61M 25/09* | (2006.01) | |

(52) U.S. Cl.
CPC ........ *A61M 1/1008* (2014.02); *A61M 1/1001* (2014.02); *A61M 1/125* (2014.02);
(Continued)

(58) Field of Classification Search
CPC .... A61M 1/10; A61M 1/1001; A61M 1/1008; A61M 1/122; A61M 1/125;
(Continued)

(56) References Cited

U.S. PATENT DOCUMENTS 5,061,256 A   10/1991 Wampler
5,624,430 A *  4/1997 Eton ................. A61M 25/0127
                                                          606/1

(Continued)

OTHER PUBLICATIONS

International Search Report and Written Opinion for Application No. PCT/US2015/065806, dated Apr. 8, 2016, 11 pages.

*Primary Examiner* — Eugene T Wu
(74) *Attorney, Agent, or Firm* — Christopher & Weisberg, P.A.

(57) ABSTRACT

In one embodiment, the present invention is a method of positioning in a mammalian heart of a patient a blood pump including an inflow cannula, a pump housing and an outflow cannula, the method including forming an incision in a low-pressure location on the heart wall; passing the outflow cannula of the blood pump through the incision and into a left ventricle of a heart; positioning a tip of a guidewire into an aorta, distal to an aortic valve; advancing the tip through the aortic valve and into the left ventricle; connecting the tip to the outflow cannula; pulling the blood pump with the guidewire to advance at least a portion of the outflow cannula through the aortic valve and into the aorta; securing the blood pump to the heart, the aorta, or both; disconnecting the tip from the blood pump; and removing the guidewire from the patient.

13 Claims, 6 Drawing Sheets

Related U.S. Application Data

(60) Provisional application No. 62/094,193, filed on Dec. 19, 2014.

(52) U.S. Cl.
CPC ............. *A61M 25/09* (2013.01); *A61M 1/101* (2013.01); *A61M 1/122* (2014.02); *A61M 2210/127* (2013.01)

(58) Field of Classification Search
CPC   A61B 2017/00238; A61B 2017/00243; A61B 2017/00247; A61B 2017/00252; A61B 2017/00358; A61B 2017/00876; A61B 2017/12086
See application file for complete search history.

(56) References Cited

U.S. PATENT DOCUMENTS

| | | |
|---|---|---|
| 6,245,007 B1 | 6/2001 | Bedingham et al. |
| 6,769,434 B2 | 8/2004 | Liddicoat et al. |
| 7,022,100 B1 | 4/2006 | Aboul-Hosn et al. |
| 8,808,367 B2 | 8/2014 | Suri et al. |
| 2006/0155158 A1 | 7/2006 | Aboul-Hosn |
| 2009/0203957 A1 | 8/2009 | LaRose et al. |
| 2010/0217384 A1 | 8/2010 | Liddicoat et al. |
| 2012/0130164 A1 | 5/2012 | Palese et al. |
| 2013/0006261 A1 | 1/2013 | Lampropoulos et al. |

\* cited by examiner

GUIDEWIRE SYSTEM AND METHOD OF PUMP INSTALLATION USING SAME

CROSS-REFERENCE TO RELATED APPLICATION

This application is a continuation of patent application Ser. No. 14/969,805, filed Dec. 15, 2015, entitled GUIDEWIRE SYSTEM AND METHOD OF PUMP INSTALLATION USING SAME, and is related to and claims priority to U.S. Provisional Patent Application No. 62/094,193, filed Dec. 19, 2014, entitled GUIDEWIRE SYSTEM AND METHOD OF PUMP INSTALLATION USING SAME the entirety of which is incorporated herein by reference.

STATEMENT REGARDING FEDERALLY SPONSORED RESEARCH OR DEVELOPMENT n/a

TECHNICAL FIELD

The present invention relates to methods of implantation and placement of a blood pump and instrumentation and devices useful in such methods.

BACKGROUND

In certain disease states, the heart lacks sufficient pumping capacity to meet the needs of the body. This inadequacy can be alleviated by providing a mechanical pumping device referred to as a blood pump to supplement the pumping action of the heart. One common type of blood pump is a ventricular assist device ("VAD"), which is implanted into the left ventricle. Considerable effort has been devoted to providing a blood pump which can be implanted and which can remain in operation for months or years to keep the patient alive while the heart heals, or which can remain in operation permanently or until a suitable donor heart becomes available if the heart does not heal.

The blood pump is typically connected to the heart, most commonly to the left ventricle (as a VAD) and positioned such that an intake cannula or opening is positioned in the left ventricle while the outflow cannula or opening is positioned at or through the aortic valve to supplement the pumping action of the left ventricle. Other blood pumps can be positioned through the aortic valve or within the aorta itself. Such blood pumps include, for example, the Longhorn Pump (HeartWare, Inc., Miami Lakes, Fla.) which is the subject of U.S. Pat. No. 8,852,072, also owned by the applicant and assignee of this application, the entirety of which is incorporated by reference herein as if fully set forth herein.

Figure 1:
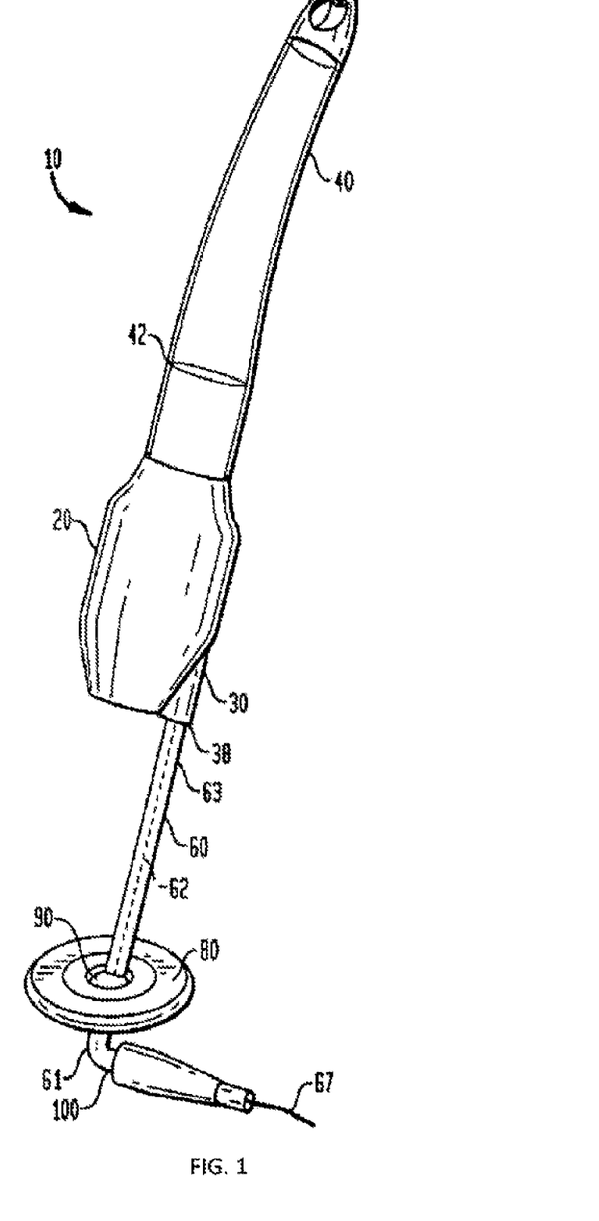
FIG. 1 illustrates an example of a blood pump for use in the present invention.
Figure 2:
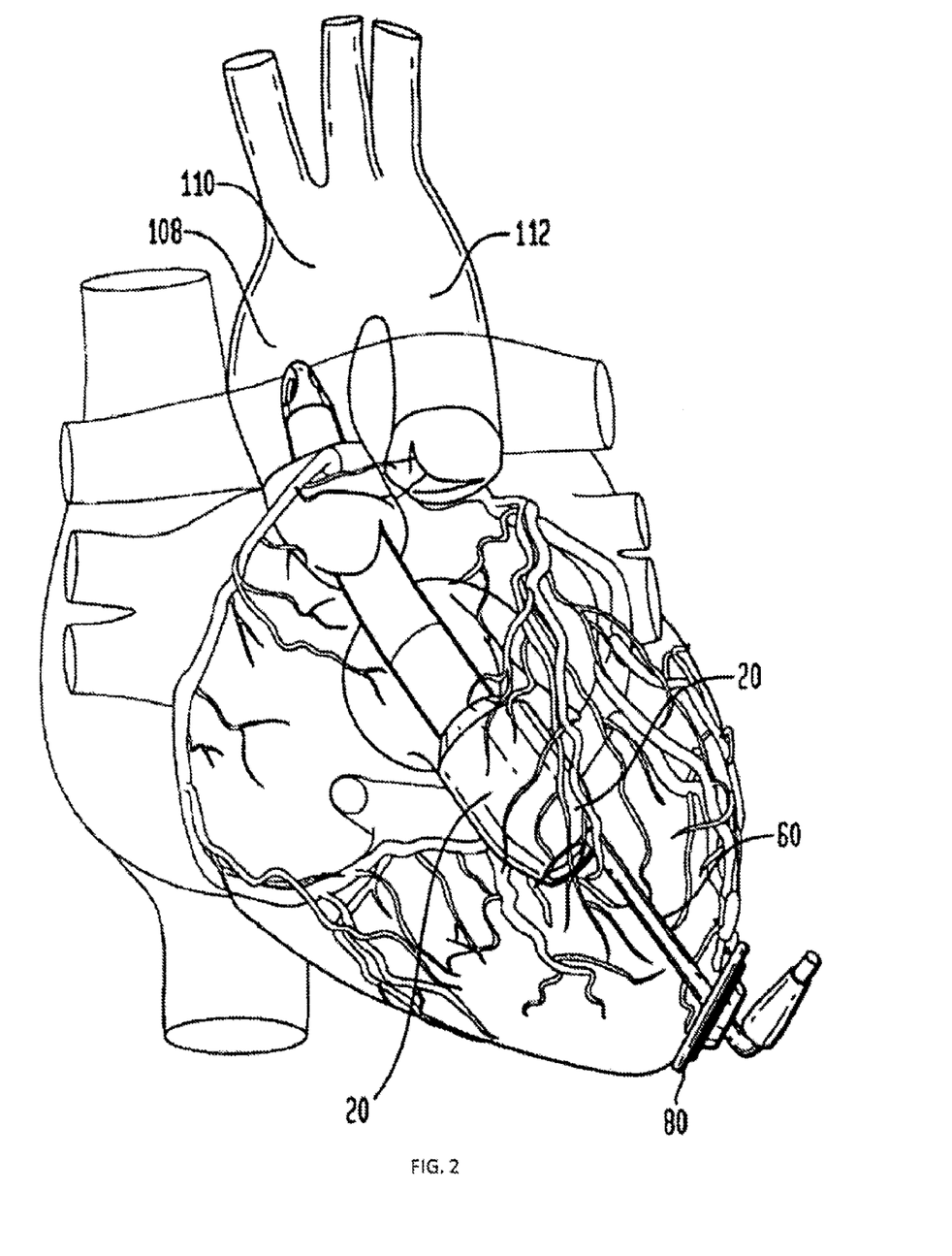
FIG. 2 illustrates an example of the intended positioning of a blood pump within a patient's vasculature.

As illustrated in FIGS. 1 and 2, reproduced from the '072 patent, a blood pump, or specifically a VAD in this instance, such as the Longhorn Pump 20, may be positioned through the apex of the heart and into the left ventricle. The outflow cannula 40 is then positioned through the aortic valve and into the ascending aorta 108.

However, difficulties arise in positioning the outflow cannula through the aortic valve. In particular, the risk of injuring the aortic valve and/or the related anatomy during placement is high, and as such a highly skilled surgeon is required to ensure safe and proper placement. Additionally, there is a risk that, during placement, the cannula instead passes into and through the mitral valve or other anatomy, causing unnecessary harm and adding complexity to the procedure. Therefore, a need exists for improved instrumentation and methods to minimize the risk associated with the placement of a blood pump in the heart, and particularly through a valve such as the aortic valve.

SUMMARY

Often times, a blood pump is of a size such that it cannot be delivered through a patient's vasculature (e.g., transfemorally or transaortically), but instead must be delivered through the wall of the heart (e.g., transapically). While transapical approaches are well known, complications can arise where the blood pump is intended to be positioned in a particularly fragile or difficult to access aspect of the vasculature, such as through a heart valve. In such instances, extreme care must be taken to avoid unnecessary contact and/or injury to any aspect of the heart valve, such as the chordae tendonae, the valve annulus or the valve leaflets themselves.

Thus, the present invention is generally directed to a system and method of placing a blood pump within a patient's vasculature, and in particular, positioning at least a portion of the blood pump through a heart valve.

In one embodiment, the present invention includes a blood pump system for use within a vasculature of a patient, including a guidewire and a blood pump. The guidewire has a tip and a first engagement feature on the tip. The engagement feature is adapted to engage the blood pump. The engagement feature can engage any aspect of the blood pump, such as a second engagement feature on the blood pump. For example, the blood pump can include an elongated outflow cannula, a pump housing and an inflow cannula or aperture. In this example, the elongated outflow cannula has the second engagement feature, a length between a pump outlet on the pump housing, a cannula tip, and a cannula diameter along at least a portion of the length. Continuing with this example, the pump housing has a housing diameter which is larger than the cannula diameter. Further, the first engagement feature is adapted to connect with the second engagement feature when the guidewire and blood pump are positioned within the vasculature.

In another embodiment, the present invention is a method of positioning a blood pump in a mammalian vasculature, the vasculature including a heart having a heart wall and a heart chamber, a heart valve, and a portion of the vasculature extending from the heart valve away from the heart, the method comprising the steps of: obtaining the blood pump, the blood pump including an elongated first cannula, a pump housing and a second cannula; passing the first cannula through an incision at a low-pressure location on the heart wall and into the heart chamber; positioning a tip of a guidewire into the portion of the vasculature, distal to the heart valve; advancing the tip through the heart valve and into the heart chamber; connecting the tip to the outflow cannula; pulling the blood pump with the guidewire to advance at least a portion of the first cannula through the heart valve and into the portion of the vasculature; securing the blood pump to the heart wall, the portion of the vasculature, or both; disconnecting the tip from the blood pump; and removing the guidewire from the patient.

In a further embodiment, the present invention includes a method of positioning in a mammalian heart of a patient a blood pump including an inflow cannula, a pump housing and an outflow cannula, the method including the steps of: forming an incision in a low-pressure location on the heart wall; passing the outflow cannula of the blood pump through the incision and into a left ventricle of a heart; positioning a tip of a guidewire into an aorta, distal to an aortic valve; advancing the tip through the aortic valve and into the left ventricle; connecting the tip to the outflow cannula; pulling the blood pump with the guidewire to advance at least a portion of the outflow cannula through the aortic valve and into the aorta; securing the blood pump to the heart, the aorta, or both; disconnecting the tip from the blood pump; and removing the guidewire from the patient.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION

As used herein unless stated otherwise, the term "proximal" means closer to the heart, and the term "distal" means further from the heart. The terms "about," "generally" and "substantially" are intended to mean that slight deviations from absolute are included within the scope of the term so modified.

The present invention relates to the placement of a blood pump within the vasculature of a mammalian patient, the vasculature including a heart having a heart wall and a heart chamber, a heart valve, and a portion of the vasculature extending from the heart valve away from the heart. While the present invention can be used to position a blood pump in a variety of positions within such a vasculature, for ease of discussion, the following embodiments will be discussed as to the exemplary method (illustrated in FIGS. 3-6) of positioning a portion of a blood pump, or VAD, from the left ventricle 100 through the aortic valve 105 and into the aorta 108 of a human vasculature.

Figure 3:
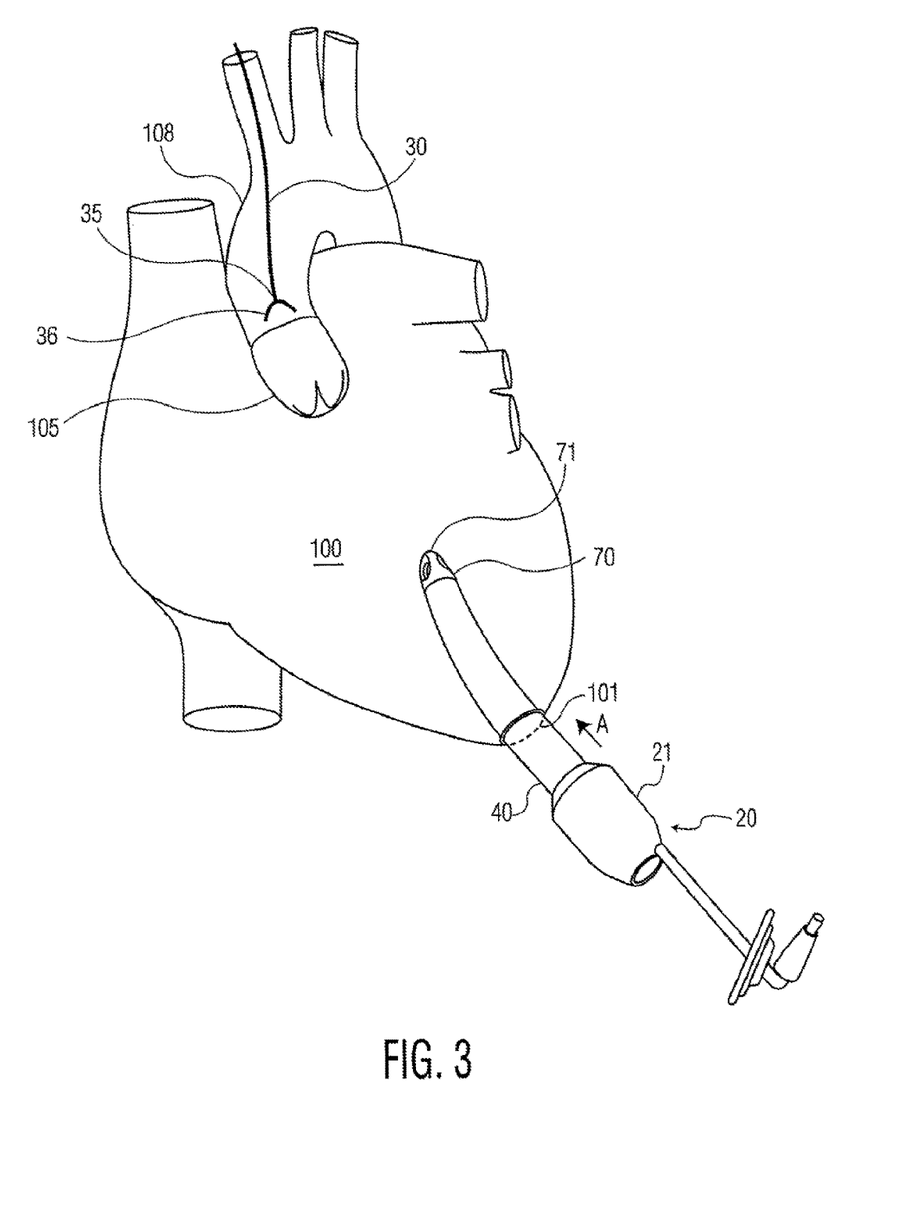
FIGS. 3 and 4 illustrate initial steps of one embodiment of a method of the present invention whereby a blood pump and guidewire approach one another within a chamber of a heart.

In one embodiment, as illustrated in FIGS. 1 and 3, the VAD 20, such as Longhorn Pump 20 discussed above, includes a first elongated cannula 40, a pump housing 21 (or labeled as "20" in FIGS. 1 and 2) and an optional second cannula (not shown) extending from the pump housing opposite the first cannula. A guidewire engagement feature 71 is located on the VAD, for example, as illustrated in FIG. 3, on a tip 70 of the cannula 40. However, the engagement feature 71 may be positioned anywhere on the VAD 20 as desired. As illustrated, the first cannula 40 is an outflow cannula and the second cannula (not shown) is an inflow cannula such that the blood pump is suitable for providing assistance to the left ventricle 100 of the heart, in that the outflow cannula 40 directs blood flow into the aorta 108. As illustrated in this embodiment, the pump housing 21 has a larger diameter than the cannula 40, such that, for example, the cannula 40 can be positioned through the aortic valve but the pump housing 21 cannot be so positioned.

Continuing with this embodiment, the present invention also includes a guidewire 30 having a length suitable for use in the vasculature of a mammal, such as a human vasculature. The length may be sufficient to allow for transaortic implantation, transfemoral implantation, or the like. The guidewire 30 includes a tip 35 which has a VAD engagement feature 36 thereon. The guidewire 30 may be constructed as is generally known in the art using Nitinol or other such biocompatible material.

In use, the VAD engagement feature 36 is adapted to releasably engage or connect to the guidewire engagement feature 71 on cannula 40. The engagement features 71, 36 preferably utilize a magnetic attractive force to join together, though other connection techniques may also be used such as a press-fit engagement, a hook and eyelet engagement, a pincer engagement, or the like. Essentially, any technique may be used which is suitable to releasably engage the engagement features 71, 36 to one another. For example, as discussed below, the technique must be suitable for engagement of the engagement features in situ, e.g., within the left ventricle of the heart, and releasable following positioning of the VAD 20 into its final, implanted position.

The VAD 20 and guidewire 30 may, in one embodiment, be a system for use within the vasculature of the patient. In another embodiment, the VAD 20 may be part of a kit including multiple guidewires 30 which may, for example, have various lengths for use depending on the type of approach desired by an operator (e.g., transaortic versus transfemoral).

The blood pump 20 and guidewire 30 may be used in various methods to position the blood pump in the vasculature of a patient in need thereof. For ease of reference, the exemplary method described below, and illustrated in FIGS. 3-6, focuses on the positioning of a portion of the VAD through the aortic valve and into the aorta. However, the method may be used in other anatomical locations of the vasculature.

In this embodiment, FIG. 3 illustrates the initial positioning of the VAD 20 and guidewire 30. The outflow cannula 40 of VAD 20 is positioned through an incision made at a low-pressure location on the wall of the heart, for example, at the apex 101 of the heart, and into the left ventricle 100. This positioning is designated by arrow A.

Similarly, as illustrated in FIG. 3, the tip 35 of the guidewire 30 is positioned through an incision made in the vasculature (e.g., the aorta, femoral artery, or the like) and is fed through the vasculature and to the aortic valve 105. The tip 35 is then positioned through the valve and into the left ventricle 100. This positioning is designated by arrow B. In navigating the guidewire 30 through the aortic valve, from the downstream or distal direction, the operator should take care to avoid the anatomy of the valve, including the leaflets, chordae tendonae, valve annulus, and the like. The small dimensions of the guidewire, which are markedly smaller than the dimensions of the VAD 20 itself, simplify this maneuver which should allow the operator to find a clear path through the valve structure that avoids any unnecessary damage to the anatomy.

Figure 4:
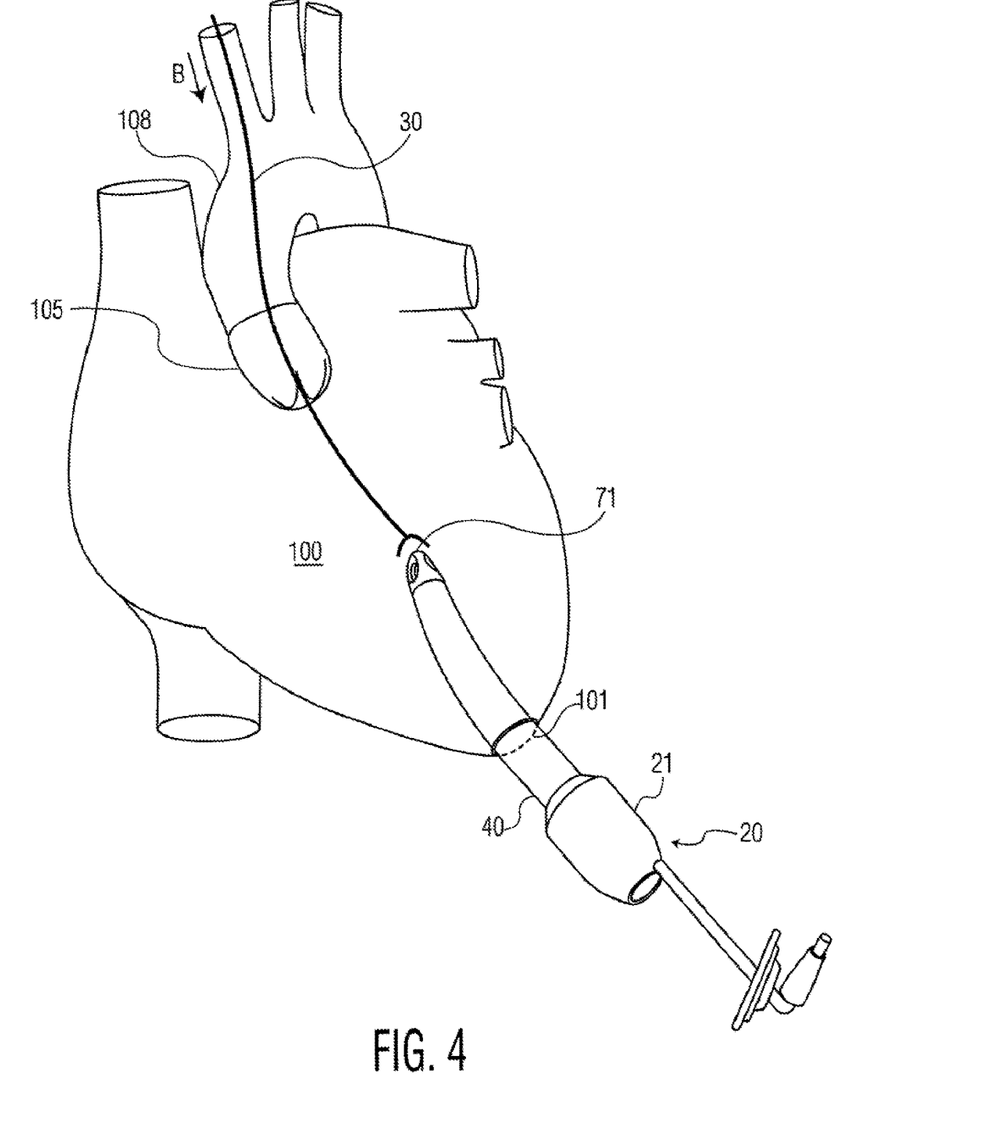

With both the tip 35 of the guidewire 30 and the tip 70 of the outflow cannula 40 positioned in the left ventricle, as illustrated in FIG. 4, the VAD engagement feature 36 is releasably engaged to the guidewire engagement feature 71. Preferably, the engagement features 71, 36 have a magnetic attraction, such that this engagement step is achieved by approximating the engagement features near one another and allowing the magnetic attractive forces to connect the engagement features together. If another connection technique is used instead of magnetic attraction, the operator can maneuver the guidewire and VAD relative one another to achieve the connection of the engagement features 71, 36 inside the left ventricle 100.

Figure 5:
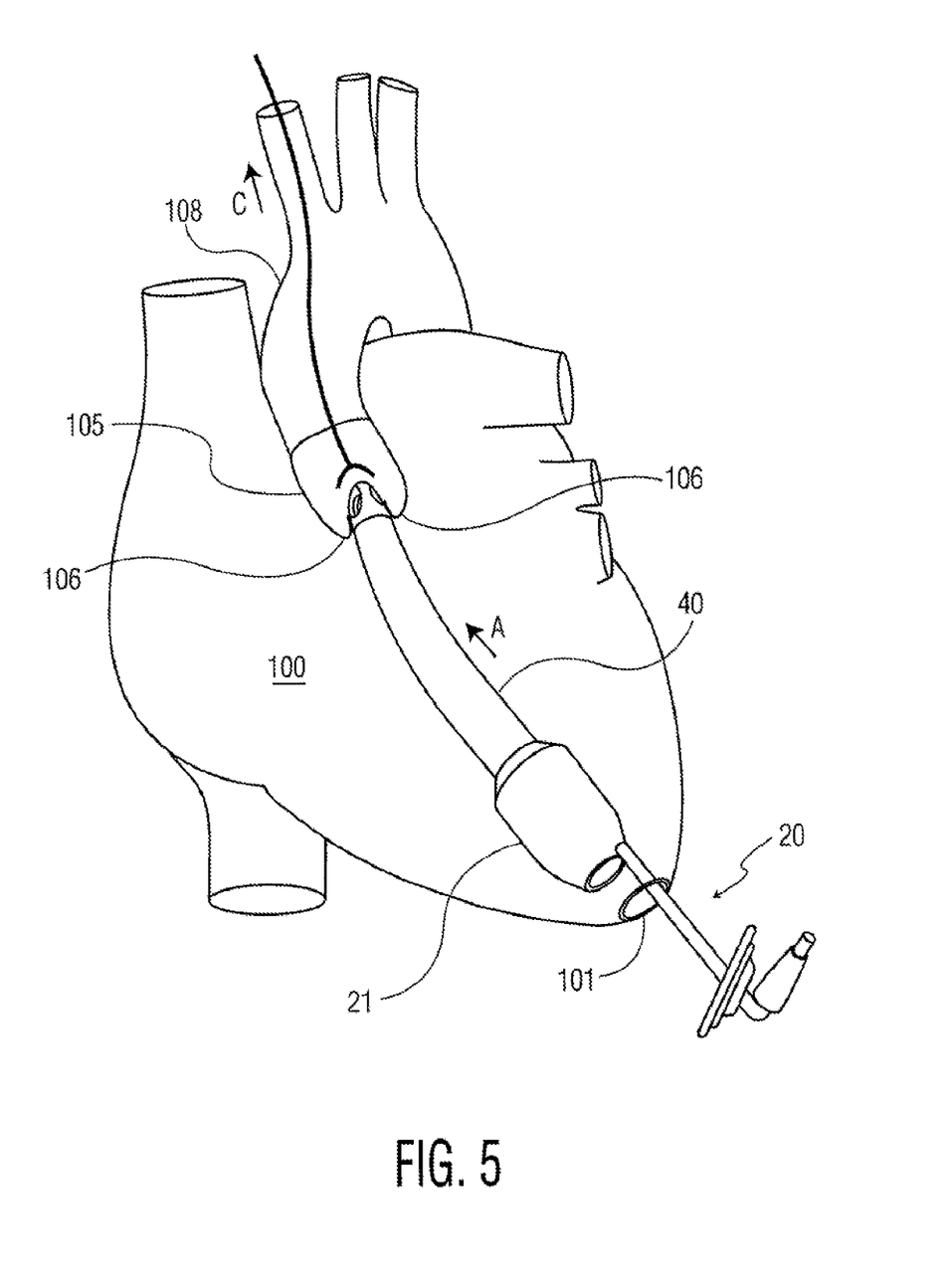
FIG. 5 illustrates a further step of the embodiment of FIGS. 3 and 4, whereby a portion of the blood pump is pulled through a heart valve and into a portion of the vasculature.

FIG. 5 illustrates the guidewire 30 pulling the VAD, in the direction of arrows A and C, such that the cannula 40 moves towards and through the aortic valve and into the aorta. Since the guidewire 30 was already positioned along a path that imparted minimal damage to the valve structure, the cannula 40 likewise can follow the guidewire into an optimal position centered among the leaflets 106 of the aortic valve. Furthermore, the use of the guidewire to pull the VAD into this position eliminates the risk of potential improper placement of the cannula into, for example, the mitral valve or another anatomical location.

Figure 6:
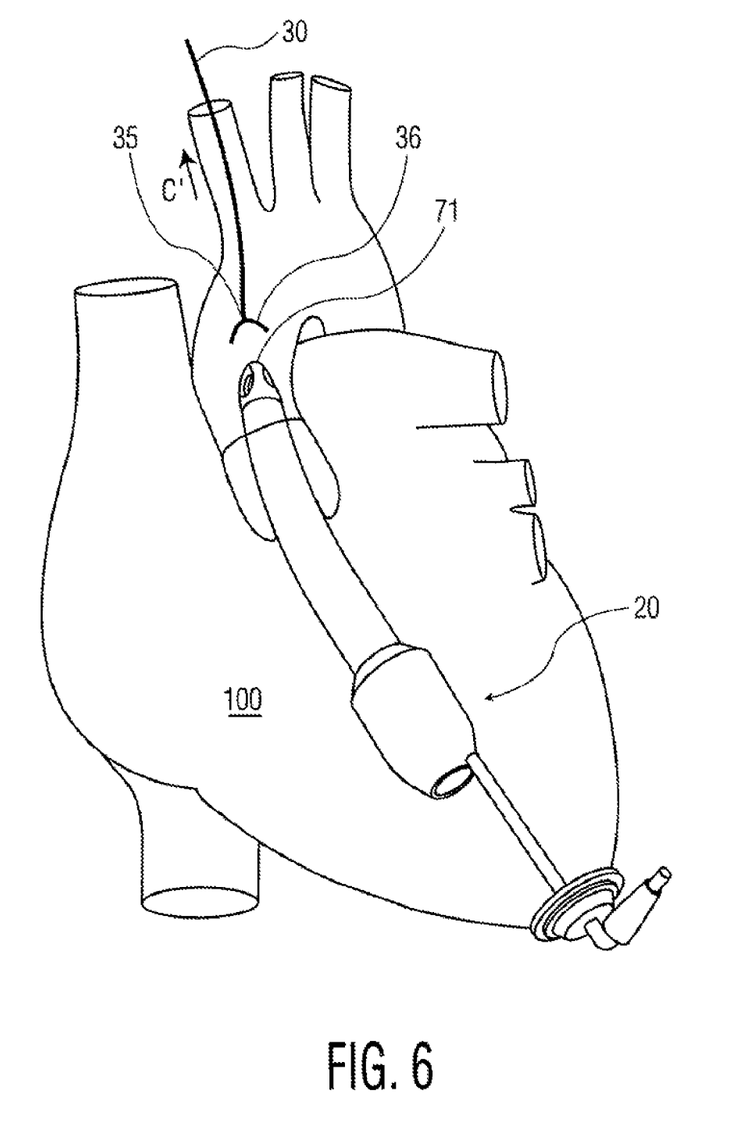
FIG. 6 illustrates still a further step of the embodiment of FIGS. 3-5, whereby the heart pump is finally positioned within the heart chamber and a portion of the vasculature, and the guidewire is disconnected from the heart pump.

The guidewire pulls the VAD until, for example, in the case of the Longhorn Pump illustrated, a ring 80 abuts the apex of the heart, as illustrated in FIGS. 2 and 6. With the ring 80 abutting the apex 101 of the heart, the ring 80 may be secured to the apex, thereby securing the VAD 20 in position, as detailed in the '072 patent. With the VAD in the proper position (and either before or after securing the ring to the apex of the heart), the guidewire is disconnected from the VAD 20. Disconnection or release of the engagement features 71, 36 may be performed in any manner, typically determined by the type of connection technique used. For example, if the magnetic connection is used, the VAD 20 is simply held in place while the guidewire 30 is pulled in the direction of arrow C' with a force sufficient to overcome the magnetic force holding the engagement features 71, 36 together. With the guidewire disconnected, the operator continues to pull the guidewire in direction C' to remove the guidewire from the vasculature of the patient. The incisions are closed and the implantation is complete.

Such a method of use of the present invention as described above provides a method of implanting a blood pump which cannot be delivered to the heart transvascularly, typically due to the size of the pump, but still must be positioned, at least partially, in the vasculature and outside the chambers of the heart. In such instances, using a guidewire to direct the blood pump to the proper anatomical location (e.g., through an appropriate heart valve) ensures proper positioning of the blood pump and minimizes the risk of harming anatomical structures.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

What is claimed is:

1. A method of positioning a blood pump in a mammalian vasculature, the vasculature including a heart having a heart wall and a heart chamber, a heart valve, and a portion of the vasculature extending from the heart valve away from the heart, comprising:
   advancing a first cannula of the blood pump through an incision on the heart wall into the heart chamber, the blood pump including a pump housing and a second cannula;
   positioning a tip of a guidewire into the portion of the vasculature, distal to the heart valve;
   advancing the tip through the heart valve and into the heart chamber;
   connecting the tip to the first cannula; and
   pulling the blood pump with the guidewire to advance at least a portion of the first cannula through the heart valve and into the portion of the vasculature.

2. The method of claim 1, wherein the heart chamber is the left ventricle and the portion of the vasculature is a portion of the aorta extending from the aortic valve, wherein the incision formed during the advancing step is formed at an apex of the heart.

3. The method of claim 2, wherein positioning the tip of the guidewire into the portion of the vasculature distal to the heart valve includes positioning the tip of the guidewire into the femoral artery and advancing the tip through the vasculature of the patient to the aorta.

4. The method of claim 1, wherein the tip of the guidewire includes a first engagement feature and at least a portion of the first cannula includes a second engagement feature, and wherein connecting the tip to the first cannula includes connecting the first engagement feature to the second engagement feature.

5. The method of claim 4, wherein the first engagement feature includes a magnetic element and the second engagement feature includes an opposing magnetic element, and wherein connecting the tip to the first cannula includes advancing the tip to a position adjacent to the first cannula.

6. The method of claim 1, further including disconnecting the tip from the blood pump by application of force on the guidewire in a distal direction away from the blood pump.

7. A method of positioning in a mammalian heart of a patient a blood pump including an inflow cannula, a pump housing, and an outflow cannula, the method comprising:
   forming an incision on the heart wall;
   passing the outflow cannula of the blood pump through the incision and into a left ventricle of the heart;
   positioning a tip of a guidewire into an aorta, distal to an aortic valve;
   connecting the tip to the outflow cannula; and
   pulling the blood pump with the guidewire to advance at least a portion of the outflow cannula through the aortic valve and into the aorta.

8. The method of claim 7, wherein positioning the tip of the guidewire into the aorta includes positioning the tip of the guidewire into the femoral artery and advancing the tip through the vasculature of the patient to the aorta.

9. The method of claim 7, further including securing the blood pump to an apex of the heart.

10. The method of claim 7, further including securing the pump housing on the heart wall.

11. The method of claim 7, wherein the tip of the guidewire includes a first engagement feature and at least a portion of the outflow cannula includes a second engagement feature, wherein connecting the tip to the outflow cannula includes connecting the first engagement feature to the second engagement feature.

12. The method of claim 11, wherein the first engagement feature includes a magnetic element and the second engagement feature includes an opposing magnetic element, and wherein connecting the tip to the outflow cannula further includes advancing the tip to a position adjacent to the outflow cannula.

13. The method of claim 7, further including disconnecting the tip from the blood pump by application of force on the guidewire in a distal direction away from the blood pump.

* * * * *